United States Patent [19]

Froment et al.

[11] Patent Number: 5,672,796
[45] Date of Patent: Sep. 30, 1997

[54] CATALYST AND PROCESS FOR HYDROCARBON AROMATIZATION

[75] Inventors: Gilbert Fernand Alphonse Froment, Martens Latem; Wilfried Jozef Hippolyte Dehertog, Tervuren, both of Belgium

[73] Assignee: Amoco Corporation, Chicago, Ill.

[21] Appl. No.: 574,120

[22] Filed: Dec. 18, 1995

Related U.S. Application Data

[63] Continuation of Ser. No. 252,746, Jun. 2, 1994, abandoned, which is a continuation of Ser. No. 126,117, Sep. 23, 1993, abandoned, which is a continuation of Ser. No. 952,922, Sep. 28, 1992, abandoned, which is a continuation of Ser. No. 835,228, Feb. 13, 1992, abandoned.

[51] Int. Cl.[6] .............................. C07C 15/00; B01J 29/06
[52] U.S. Cl. ............................ 585/419; 585/407; 502/66
[58] Field of Search .................................... 585/407, 419

[56] References Cited

U.S. PATENT DOCUMENTS

| | | | |
|---|---|---|---|
| 3,926,782 | 12/1975 | Plank et al. | 208/135 |
| 4,276,151 | 6/1981 | Plank et al. | 208/138 |
| 4,416,806 | 11/1983 | Bernard et al. | 502/74 |
| 4,665,267 | 5/1987 | Barri | 585/660 |
| 4,766,165 | 8/1988 | Kress et al. | 524/140 |
| 4,766,265 | 8/1988 | Desmond et al. | 585/415 |
| 4,788,364 | 11/1988 | Harandi | 585/312 |
| 4,795,732 | 1/1989 | Barri | 502/223 |
| 4,835,336 | 5/1989 | McCullen | 585/419 |
| 4,861,932 | 8/1989 | Chen et al. | 585/412 |
| 5,026,938 | 6/1991 | Shum | 585/417 |
| 5,108,969 | 4/1992 | Del Rossi et al. | 502/66 |

FOREIGN PATENT DOCUMENTS

| | | | |
|---|---|---|---|
| 1150712 | 7/1983 | Canada | 502/61 |

OTHER PUBLICATIONS

"Propane Conversion to Aromatic Hydrocarbons on Pt/H-ZSM-5 Catalysts" *Journal of Catalysis*, vol. 90, pp. 366-367 (1984).

*Primary Examiner*—Glenn A. Caldarola
*Assistant Examiner*—In Suk Bullock
*Attorney, Agent, or Firm*—G. Byron Stover; Frederick S. Jerome; Wallace L. Oliver

[57] ABSTRACT

A catalyst and process is described for aromatizing one or more $C_3$ to $C_6$ saturated hydrocarbon to a product low in methane and essentially containing ethane or ethane and propane and aromatic hydrocarbons. A partially sulfided, Pt/Re loaded, essentially hydrogen-form, crystalline aluminosilicate molecular sieve exhibiting the MFI structure and having a Si/Al ratio between about 40 and about 600 is shown to have an excellent catalyst lifetime and favor low methane production, high conversion and high selectivity to benzene, toluene and xylenes and ethane or ethane and propane.

20 Claims, 1 Drawing Sheet

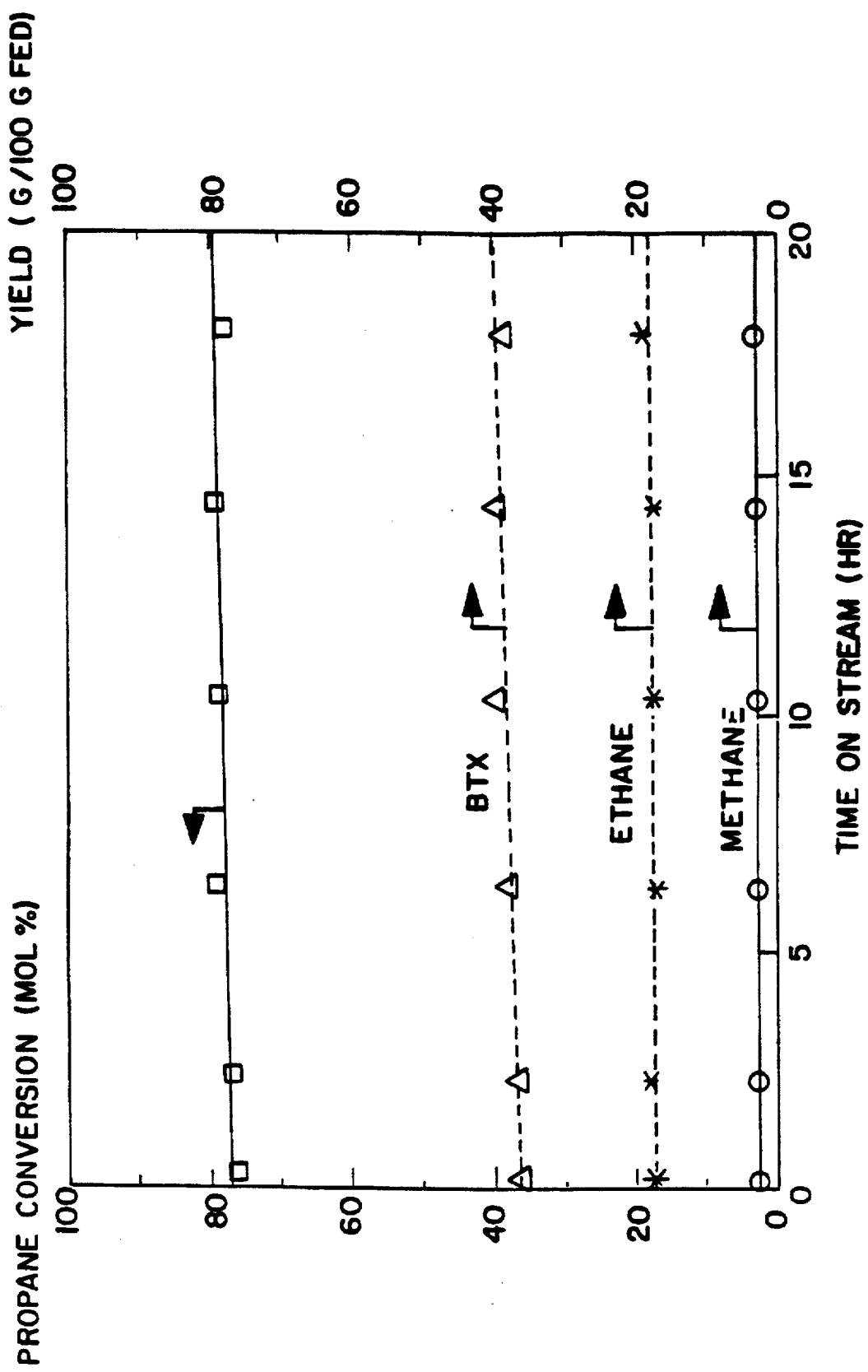

CATALYST AND PROCESS FOR HYDROCARBON AROMATIZATION

This is a continuation of application Ser. No. 08/252,746, filed Jun. 2, 1994, which is a continuation of application Ser. No. 08/126,117, filed Sep. 23, 1993, which is a continuation of application Ser. No. 07/952,922, filed Sep. 28, 1992, which is a continuation of application Ser. No. 07/835,228, filed Feb. 13, 1992 (all now abandoned).

BACKGROUND OF THE INVENTION

This invention relates to a one stage process for the aromatization of a feed containing one or more $C_3$ to $C_6$ saturated hydrocarbons to primarily an aromatic rich, low-methane-containing hydrocarbon product over a partially sulfided, Pt/Re-containing crystalline aluminosilicate molecular sieve catalyst exhibiting the MFI crystal structure and, more preferably, to a one stage process for the aromatization of a feed containing one or more $C_3$ to $C_6$ saturated hydrocarbons to an aromatic rich, low-methane-containing hydrocarbon product over a partially sulfided, Pt/Re-containing crystalline aluminosilicate molecular sieve having a Si/Al ratio between about 40 and about 600 which exhibits the MFI crystal structure.

In the past various molecular sieve compositions natural and synthetic have been found to be useful for a number of hydrocarbon conversion reactions. Among the sieves used are Types A, X, Y and those of the MFI crystal structure. Representative of the last group are ZSM-5 and AMS borosilicate molecular sieves.

The aromatization of mainly saturated hydrocarbon feeds over heavy-metal-containing aluminosilicates is an area of substantial commercial interest as such catalysts are capable of converting the feed to mixtures rich in aromatic hydrocarbons. For example, U.S. Pat. No. 4,766,165 to Chevron uses a HZSM-5 aluminosilicate, gallosilicate or borosilicate containing rhenium and, inter alia, platinum for the aromatization of ethane. U.S. Pat. No. 4,788,364 to Mobil describes a two step process for the conversion of $C_2$ to $C_{10}$ alkane-rich feeds over various ZSM catalysts having a Si/Al ratio of at least 12 which can contain elements such as P, Ga, Sn, Re, Zn, Pt and Cu to obtain in a first step oligomerizable olefinic hydrocarbons and aromatics which are converted in the second step to gasoline boiling range aliphatic and aromatic hydrocarbons. The two step process involves two reactors with an intermediate separation step to remove $C_6+$ aromatics. Removal also insures that less aromatics which could lead to the formation of coke precursors are fed to the second step catalyst. In U.S. Pat. No. 4,835,336 to Mobil, non-aromatic $C_6$–$C_{12}$ hydrocarbons are converted to aromatics over a ZSM-5 catalyst containing a platinum group metal (Pt, Pd, Ir, Os, Rh or Ru). The catalysts were sulfided to suppress hydrogenolysis and increase aromatic selectivity. Mobil in European Patent No. 0186479, Example 7, describes the reforming of a naphtha to a product containing benzene and toluene over a ZSM-5 catalyst containing 0.01–10 wt. % platinum and 0.01–5 wt. % rhenium.

Now, by partially-sulfiding, a Pt/Re-loaded, MFI crystal structure crystalline aluminosilicate molecular sieve, a catalyst of substantially increased catalyst run length can be made which will selectively aromatize a $C_3$ to $C_6$ saturated hydrocarbon, such as propane, to a benzene, toluene and xylene (BTX) rich product containing only small amounts of methane while producing substantial amounts of ethane or ethane and propane (depending upon the hydrocarbon fed).

SUMMARY OF THE INVENTION

The invention contained herein is a partially sulfided, Pt/Re-loaded, essentially hydrogen-form, crystalline alumi- nosilicate molecular sieve exhibiting the MFI crystal structure and having a Si/Al ratio between about 40 and about 600 which provides an x-ray pattern comprising the following interplanar spacings and assigned strengths:

| Interplanar Spacing[1] d(Angstroms) | Assigned[2] Strength | Interplanar Spacing[1] d(Angstroms) | Assigned[2] Strength |
|---|---|---|---|
| 11.109 ± 0.05 | VS | 3.810 ± 0.04 | M |
| 10.019 ± 0.05 | M | 3.709 ± 0.04 | MW |
| 9.925 ± 0.05 | S | 3.743 ± 0.04 | W |
| 9.703 ± 0.05 | W | 3.638 ± 0.04 | W |
| 6.341 ± 0.04 | W | 3.131 ± 0.04 | M |
| 3.843 ± 0.04 | M | 1.918 ± 0.03 | MW |

[1] copper K alpha radiation
[2] VW = very weak W = weak M = medium MS = medium strong S = strong VS = very strong In another aspect, the invention is a one stage process which contacts under hydrocarbon conversion conditions a feed comprising at least one $C_3$ to $C_6$ alkane with a partially sulfided, Pt/Re-loaded, essentially hydrogen-form, crystalline aluminosilicate molecular sieve exhibiting the MFI crystal structure and having a Si/Al ratio between about 40 and 600 which provides an x-ray pattern comprising the following interplanar spacings and assigned strengths:

| Interplanar Spacing[1] d(Angstroms) | Assigned[2] Strength | Interplanar Spacing[1] d(Angstroms) | Assigned[2] Strength |
|---|---|---|---|
| 11.109 ± 0.05 | VS | 3.810 ± 0.04 | M |
| 10.019 ± 0.05 | M | 3.709 ± 0.04 | MW |
| 9.925 ± 0.05 | S | 3.743 ± 0.04 | W |
| 9.703 ± 0.05 | W | 3.638 ± 0.04 | W |
| 6.341 ± 0.04 | W | 3.131 ± 0.04 | M |
| 3.843 ± 0.04 | M | 1.918 ± 0.03 | MW |

[1] copper K alpha radiation
[2] VW = very weak W = weak M = medium MS = medium strong S = strong VS = very strong to form a low-methane-containing hydrocarbon product which is rich in aromatic hydrocarbons.

BRIEF DESCRIPTION OF THE DRAWING

FIG. 1 shows propane conversion as a function of time on stream for the catalyzed aromatization of propane at a weight hourly space velocity (WHSV) of 0.4 $hr^{-1}$, 490° C. and 1.05 bar. The yields on a g/100 g of feed basis for methane, ethane and BTX products are also shown. The catalyst is a partially sulfided, Pt/Re-containing, crystalline aluminosilicate molecular sieve essentially in the hydrogen form having the MFI crystal structure and a Si/Al ratio of about 60.

DETAILED DESCRIPTION OF THE INVENTION

The hydrocarbon feedstock which is useful in the aromatization process described herein is one or more $C_3$ to $C_6$ alkane. More preferably it is propane, butane, hexane or a mixture of two or more of such saturated hydrocarbons. Most preferably it is propane.

The molecular sieve useful in this invention can be prepared by crystallizing an aqueous mixture, at a controlled pH, of sources for cations, an oxide of aluminum, an oxide of silicon, and an organic template compound.

Typically, the mol ratios of the various reactants can be varied to produce the crystalline aluminosilicates of this invention. Specifically, the mol ratios of the initial reactant concentrations are indicated below:

| Reactants | Broad | Preferred | Most Preferred |
|---|---|---|---|
| $SiO_2/Al_2O_3$ | 5–400 | 10–150 | 40–120 |
| $R_2O^{y}/[R_2O^+ + M_2n^o]$ | 0.1–1.0 | 0.2–0.97 | 0.2–0.9 |
| $OH^-/SiO_2$ | 0.01–11 | 0.02–2 | 0.03–1 |
| $H_2O/OH^-$ | 10–4000 | 10–500 | 10–500 | wherein R is an organic compound and M is at least one cation having the oxidation state n, such as an alkali or an alkaline earth metal cation or hydrogen. By regulation of the quantity of aluminum (represented a $Al_2O_3$) in the reaction mixture, it is possible to vary the $SiO_2/Al_2O_3$ molar ratio in the final product.

More specifically, the sieve material useful in the present invention may be prepared by mixing a base, an aluminum oxide source, and an organic template compound in water (preferably distilled or deionized). The order of addition usually is not critical although a typical procedure is to dissolve base and sodium aluminate in water and then add the template compound. Generally, the silicon oxide compound is then added with intensive mixing such as that performed in a Waring blendor and the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10 to about 11.

Examples of materials affording silicon oxide useful in this invention include silicic acid, sodium silicate, tetraalkyl silicates and Aerosil-380, a product of Degussa Ag. Typically, the oxide of aluminum source is sodium aluminate.

Cations useful in formation of crystalline aluminosilicate include alkali metal and alkaline earth metal cations such as sodium, potassium, lithium, calcium and magnesium. Ammonium cations may be used alone or in conjunction with such metal cations. Since basic conditions are required for crystallization of the molecular sieve of this invention, the source of such cation usually is a hydroxide such as sodium hydroxide. If a base such as ethylenediamine is used, the hydrogen form of the sieve can be made directly.

Organic templates useful in preparing crystalline aluminosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

In a more preferred description of a typical preparation of this invention, suitable quantities of sodium hydroxide and silica are dissolved with intense mixing in distilled or deionized water followed by addition of the organic template. The sodium aluminate is then slowly added with mixing. The pH is adjusted to about 10.5±0.05 using a compatible acid such as sulfuric acid or base.

Alternatively and more preferably, crystalline aluminosilicate molecular sieve can be prepared by crystallizing a mixture of sources for an oxide of silicon, an oxide of aluminum, an alkyl ammonium compound and ethylenediamine such that the initial reactant molar ratios of water to silica range from about 1 to about 20, preferably about 3 to about 10 and most preferably from about 4 to about 6. In addition, preferable molar ratios for initial reactant silica to oxide of aluminum range from about 4 to about 150, more preferably from about 5 to about 120 and most preferably from about 5 to about 80. The molar ratio of ethylenediamine to silicon oxide should be above about 0.01, typically below 11, preferably between about 0.01 and about 2.0 and most preferably between about 0.02 and 1. The molar ratio of alkylammonium compound, such as tetra-n-propylammonium bromide, to silicon oxide can range from 0 to about 1 or above, typically above about 0.005, preferably about 0.01 to about 0.1, more preferably about 0.01 to about 0.1 and most preferably about 0.02 to about 0.08.

The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about one to about seven days, at a temperature ranging from about 100° C. to about 250° C., preferably about 125° C. to about 200° C. The crystallizing material can be stirred or agitated as in a rocker bomb. Preferably, the crystallization temperature is maintained below the decomposition temperature of the organic template compound. Especially preferred conditions are crystallizing at about 150° C. for about two to five days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50°–225° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 260° C. to about 850° C. and preferably from about 425° C. to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 120° C. for about 16 hr and is then calcined in air in a manner such that the temperature rise does not exceed 125° C. per hr until a temperature of about 550° C. is reached. Calcination at this temperature usually is continued for about 4 to 16 hr.

Catalytically active metals are placed onto the aluminosilicate sieve by ion exchange, impregnation, a combination thereof, or other suitable contact means. Before placing the catalytically active metals on the aluminosilicate sieve, the aluminosilicate is desirably in the hydrogen form. If the sieve was prepared using a metal hydroxide, such as sodium hydroxide, the hydrogen form typically is produced by exchanging one or more times with ammonium ion, typically using ammonium nitrate, followed by drying and calcination as described above.

Ion exchange and impregnation techniques are well-known as can be understood by one skilled in the art. Typically, an aqueous solution of a soluble platinum salt such as Pt(NH$_3$)$_4$Cl$_2$ is competitively exchanged using ammonium nitrate one or more times at ambient temperature. Then a soluble rhenium compound such as a rhenium (VII) oxide, rhenium (III) chloride or ammonium perrhenate is used to impregnate the Pt-loaded sieve, preferably by the incipient wetness technique.

The amount of catalytically active platinum and rhenium placed on the aluminosilicate can vary individually from about 0.01 wt. % to about 5 wt. %, typically from about 0.1 to about 1 wt. %, and most preferable 0.1 to 0.5 wt. %. The wt. % of rhenium is preferably less than the wt. % of platinum present on the sieve. A mininum quantity of rhenium is required in order to help isolate the platinum clusters present on the sieve.

The crystalline, metal-loaded aluminosilicate molecular sieve useful in this invention can be admixed with or incorporated within various binders or matrix materials depending upon the intended process use. The crystalline aluminosilicate can be combined with active or inactive materials, synthetic or naturally-occurring zeolites, as well as inorganic or organic materials which would be useful for binding the aluminosilicate. Well-known materials include silica, alpha-alumina, magnesia, titania, zirconia, alumina sols, hydrated aluminas, clays such as bentonite or kaolin, or other binders well-known in the art. Preferably silica or alpha-alumina is used as a binder. Typically, the aluminosilicate is incorporated within a matrix material by blending with a sol of the matrix material and gelling the resulting mixture. Also, solid particles of the aluminosilicate and matrix material can be physically admixed. Typically, such aluminosilicate compositions can be pelletized or extruded into useful shapes. The crystalline aluminosilicate content can vary anywhere from a few up to 100 wt. % of the total composition. Catalytic compositions can contain about 0.1 wt. % to about 100 wt. % crystalline aluminosilicate material and preferably contain about 10 wt. % to about 95 wt. % of such material and most preferably contain about 20 wt. % to about 80 wt. % of such material.

Partial sulfiding of the catalyst, neat or composited in a binder, can be accomplished, as is known to those skilled in the art, by passing a dilute stream (about 1 vol. %) of hydrogen sulfide over the catalyst surface after reduction of the active metals present by hydrogen. Upon sulfur breakthrough, the hydrogen sulfide flow is generally stopped and replaced by hydrogen. By partial sulfiding, it is meant that the amount of sulfur on the catalyst is desirably a small fraction of the total active metals present.

Aromatization in the presence of the above-described catalyst compositions is effected by contact of a hydrocarbon feed, such as propane, at a temperature between about 300° C. and about 600° C. more preferably between about 300° C. and about 550° C. The reaction generally takes place at atmospheric pressure, but the pressure may be within the approximate range of about 1 bar to about 30 bar, more preferably between about 1 bar and about 5 bar. Reaction is suitably accomplished utilizing a weight hourly space velocity of between about 0.1 to about 100 hr$^{-1}$ and preferably between about 0.2 and about 50 hr$^{-1}$.

Aromization with the catalyst described can exhibit a long catalyst run length as the catalyst exhibits a reduced tendency to coke which is an important aspect of the invention. The aromization product consists selectively of BTX and ethane or ethane and propane (depending upon the hydrocarbon fed) together with a very low methane content. The presence of such a bimodal aromization product distribution where benzene, toluene and xylene hydrocarbons together with ethane or ethane and propane are the main products is a typical aspect of the catalyst of this invention.

The selectivity to methane in the herein described process is very low, preferably less than about 3 wt. % and more preferably less than about 1 wt. %. The selectivity to BTX hydrocarbons is preferably greater than about 30 wt. %, more preferably greater than 35 wt. %, and most preferably greater than about 45 wt. %.

The following Examples will serve to illustrate certain specific embodiments of the herein disclosed invention. These Examples should not, however, be construed as limiting the scope of the novel invention contained herein as there are many variations which may be made thereon without departing from the spirit of the disclosed invention, as those of skill in the art will recognize.

EXAMPLES

General

All percentages are wt. % unless otherwise stated. All elemental analyses were done using the Inductively Coupled Plasma (ICP) technique. Platinum dispersion values were obtained by a pulsed CO chemisorption technique after hydrogen reduction of the sample using 10% CO in helium.

The aluminosilicate molecular sieves were made generally according to example 10b on pg. 19 of Studies in Surface Science and Catalysts, Vol. 33, "Synthesis of High Silica Silica Aluminosilicate Zeolites" Elsevier Press (1987) by Jacobs and Martens.

Catalytic runs were carried out by passing hydrocarbon feed through about a 10 cm length of catalyst contained in a ceramic tube plug flow reactor (520 mm by 18 mm i.d.) fitted with a sliding thermocouple to monitor the temperature profile. The products of the aromization reactor were passed on line through a gas chromtograph fitted with a flame ionization detector for hydrocarbon analysis and a thermal conductivity detector for permanent gases (H$_2$, N$_2$) and C$_1$–C$_4$ hydrocarbons.

Example 1

A 4.8 g amount of sodium hydroxide was dissolved in 120 ml of doubly distilled (DD) water and 33.3 g of silica (Aerosil-380) added with continuous mixing to form a homogeneous gel. A 7.44 g amount of tetrapropylammonium bromide dissolved in 114 ml of DD water was added to the gel followed by a solution made from 1.026 g of NaAlO$_2$.H$_2$O in 30 ml of DD water while continuously mixing the gel. Sulfuric acid (95%) was added to the mix until the pH was 10 followed by 100 ml of DD water added with thorough mixing. The result was then added to a 200 ml autoclave and heated with stirring at 150° C. for 72 hr. The autoclave was then cooled and the crystalline product filtered, washed and dried at 80° C. The resulting sodium zeolite was then calcined at 550° C. in air for 16 hr.

The calcined sodium zeolite was ion exchanged with a 1M ammonium nitrate solution (40 ml/g of calcined product) at total reflux conditions for 3 hr and then washed with DD water and dried to form the ammonium form of the zeolite.

A 5 g portion of the ammonium zeolite was suspended in a solution of 2.51 of DD water containing 1.95 g of NH$_4$NO$_3$ and 0.0172 g of tetraammineplatinum (II) chloride to make a platinum-loaded ammonium zeolite. The suspension was stirred at ambient temperature for 24 hr, filtered and the solid washed and dried. Ion exchange is preferred to impregnation because of the high activity and stability of the resulting catalyst. Executing the ion exchange competitively with ammonium nitrate renders a still more active catalyst less subject to deactivation. Rhenium was incorporated into 5 g of the Pt-loaded ammonium zeolite using the incipient wetness technique by treating with a solution of 0.0156 g of $ReCl_3$ dissolved in 2 ml of DD water and the resulting solid dried at 80° C. The result is a Pt/Re loaded ammonium zeolite containing 44% Si, 7,700 ppm Al, 55 ppm Na, 1,250 ppm Pt and 2,650 ppm Re. The Si/Al ratio is 57.1. The surface area measured by BET using nitrogen is 395 $m^2/g$ with an average pore radius of 14 Angstroms, a micropore area of 17 $m^2/g$ and a micropore volume of 0.0137 cc/g. Powder XRD shows the solid has the MFI crystal structure and a unit cell volume of 5358 cubic Angstroms.

The dried Pt/Re-loaded ammonium zeolite powder was pelletized by compressing it to 375 $kg/cm^2$ and thereafter crushing and sieving the result to 0.5 to 1.0 mm particles. The powder was then diluted 1 to 5 times with inert alumina beads before using for catalytic studies.

The partially sulfided version of the catalyst was made by passing 1 vol. percent hydrogen sulfide in hydrogen over the reduced catalyst at 400° C. until hydrogen sulfide breakthrough. It is well-known that with $Pt-Al_2O_3$ reforming-catalyst suppression of hydrogenolysis and enhancement of aromatization can only be achieved by reversibly adsorbed S on the Pt over and above that held irreversibly (P. G. Menon, G. B. Marin and G. F. Froment; Ind. Eng. Chem. Prod. Res. Dev., Vol 21, No. 1, pp. 52, 1982). With Pt/Re-$Al_2O_3$, however, strongly held sulfur suffices to efficiently suppress the hydrogenolysis. Reversibly adsorbed sulfur also suppresses the dehydrogenation reactions substantially and is therefore detrimental (P. A. Van Trimpont, G. B. Marin and G. F. Froment; Appl. Catal., 17, pp. 161, 1985). That is why the excess of sulfur was removed from the sulfided Pt/Re-loaded zeolite by flushing the catalyst with hydrogen at 400° C. until the effluent was free of hydrogen sulfide. Further stripping of sulfur was carried out by flowing hydrogen at reaction temperature. The sulfur content of the catalyst at this point by microscale high temperature sulfur determination was between about 50 to about 200 ppm. The catalyst was then flushed thoroughly with nitrogen to ensure that the catalyst surface was hydrogen-free which avoids suppression of dehydrogenation and avoids the favoring of hydrogenolysis in the initial stages of the reaction.

The complete x-ray diffraction pattern (except for reflections with intensities less than one) of the partially sulfided form of the molecular sieve is set out below:

| d-spacing | Intensity | d-spacing | Intensity |
|---|---|---|---|
| 11.1089 | 100 | 5.3481 | 2 |
| 3.1306 | 45 | 3.3408 | 2 |
| 9.9251 | 43 | 5.0129 | 2 |
| 3.8095 | 40 | 3.4729 | 2 |
| 3.8429 | 31 | 3.9963 | 2 |
| 10.0188 | 28 | 7.4090 | 2 |
| 3.7085 | 20 | 2.6014 | 1 |
| 1.9178 | 17 | 2.7261 | 1 |
| 3.7426 | 15 | 2.9591 | 1 |
| 9.7026 | 14 | 2.3907 | 1 |
| 6.3407 | 13 | 2.4109 | 1 |
| 3.6376 | 13 | 1.6666 | 1 |
| 1.6358 | 9 | 4.0710 | 1 |
| 5.9776 | 9 | 1.8688 | 1 |
| 5.5556 | 8 | 3.2426 | 1 |
| 6.6836 | 7 | 1.9482 | 1 |
| 5.6911 | 7 | 2.5085 | 1 |
| 4.9663 | 6 | 2.5823 | 1 |
| 5.9309 | 6 | 5.1230 | 1 |
| 4.2477 | 6 | 2.8579 | 1 |
| 4.3497 | 6 | 2.5649 | 1 |
| 3.2981 | 5 | 4.4428 | 1 |
| 1.9879 | 4 | 1.6583 | 1 |
| 3.0426 | 4 | 1.6561 | 1 |
| 2.9825 | 4 | 8.9506 | 1 |
| 3.4317 | 3 | 2.7789 | 1 |
| 3.3119 | 3 | 2.3798 | 1 |
| 2.0068 | 3 | 1.6719 | 1 |
| 2.9355 | 3 | 1.7526 | 1 |
| 4.5991 | 3 | 2.6519 | 1 |
| 2.9674 | 3 | 1.5625 | 1 |
| 2.4832 | 2 | 1.7655 | 1 |

$CuK\alpha$ radiation

Example 2

The alumina-bead-diluted catalyst of Example 1 was slowly heated at 30° C./hr in a reactor up to 400° C. in an air flow and held for 12 hr at 400° C. while flowing air was passed over it and the catalyst was then reduced in a hydrogen stream for 4 hr at 400° C. The result is a Pt/Re-loaded, hydrogen zeolite which is diluted by alumina. The bed is either used directly as an aromatization catalyst or first partially sulfided as set forth in Example 1. The catalytic results using a partially sulfided catalyst are shown below in Table 1.

TABLE 1

| Feed | $C_3H_8$ | $n-C_4H_{10}$ | $n-C_6H_{14}$ |
|---|---|---|---|
| T (°C.) | 490 | 440 | 440 |
| $P_t$ (bar) | 1.05 | 1.05 | 1.05 |
| WHSV ($hr^{-1}$) | 0.367 | 0.483 | 1.459 |
| Time (min) (1) | 620 | 740 | 120 |
| X (2) | 78.68 | 96.99 | 99.69 |
| Selectivity (3‡) | | | |
| $H_2$ | 7.07 | 2.47 | 5.85 |
| $CH_4$ | 3.24 | 0.78 | 0.28 |
| $C_2H_6$ | 21.88 | 11.23 | 6.10 |
| $C_2H_4$ | 0.11 | 0.0 | 0.01 |
| $C_3H_6$ | 1.50 | 0.78 | 0.38 |
| $C_3H_8$ | (5) | 47.96 | 14.84 |
| $\Sigma C_4H_8$ | 0.28 | 0.33 | 0.25 |
| $i-C_4H_{10}$ | 0.71 | 2.54 | 1.91 |
| $n-C_4H_{10}$ | 1.04 | (5) | 1.37 |
| Benzene | 9.77 | 4.58 | 2.68 |
| Toluene | 22.99 | 15.15 | 13.31 |
| Xylenes | 17.48 | 13.20 | 22.44 |
| Ethylbenzene | 0.17 | 0.0 | 0.21 |
| (4) | 13.75 | 0.66 | 29.81 |
| BTX | 50.24 | 32.92 | 38.43 |

(1) Time on stream
(2) mols converted/100 mols fed
(3) g formed/g converted for 100 g fed
(4) $C_8+$ aromatics, mainly naphthalenes and methylnaphthalenes
(5) Feed That which is claimed is:

1. A one-stage process to convert $C_3$ to $C_6$ alkanes to a low methane-containing hydrocarbon product rich in aromatics comprising:

contacting a feed comprising at least one $C_3$ to $C_6$ alkane under conversion conditions, without addition of hydrogen, with a catalyst component consisting essentially of a hydrogen-form, Pt/Re-loaded crystalline aluminosilicate molecular sieve, having the MFI crystal structure and a Si/Al ratio between about 40 to about 600, which has been partially sulfided.

2. The process of claim 1 in which the catalyst component contains about 0.01 to about 0.5 wt. % platinum and rhenium.

3. The process of claim 1 in which the catalyst component is composited with a low acidity inorganic matrix.

4. The process of claim 1 in which the matrix comprises alpha-alumina or silica.

5. The process of claim 1 in which the feed is essentially propane and the resulting hydrocarbon product essentially contains ethane and aromatic hydrocarbons.

6. The process of claim 1 in which the feed is essentially butane and the resulting hydrocarbon product essentially contains ethane, propane, and aromatic hydrocarbons.

7. The process of claim 1 in which the feed is essentially hexane and the resulting hydrocarbon product essentially contains ethane, propane, and aromatic hydrocarbons.

8. The process of claim 3 in which catalyst component is composited with about 20 to about 80 wt. % alpha-alumina matrix.

9. The process of claim 1 in which the hydrocarbon conversion conditions comprise a temperature of about 300° to about 600° C., a pressure of about 1 to about 30 bar, a weight hourly space velocity of about 0.1 to about 100 hr$^{-1}$.

10. The process of claim 9 in which the hydrocarbon conversion conditions comprise a temperature of about 300° to about 550° C., a pressure of about 1 to about 5 bar, a weight hourly space velocity of about 0.2 to about 50 hr$^{-1}$.

11. The process of claim 1 in which the selectivity to methane is less than about 3 wt. %.

12. The process of claim 1 in which the selectivity to methane is less than about 1 wt. %.

13. The process of claim 1 in which the selectivity to BTX hydrocarbons is greater than about 30 wt. %.

14. The process of claim 1 in which the selectivity to BTX hydrocarbons is greater than about 45 wt. %.

15. A one-stage process to convert $C_3$ to $C_6$ alkanes to a low-methane containing hydrocarbon product rich in aromatics comprising:

contacting a hydrocarbon feed comprising at least one $C_3$ to $C_6$ alkane under conversion conditions, without addition of hydrogen, with a catalyst component consisting essentially of a hydrogen-form, crystalline aluminosilicate molecular sieve having the MFI crystal structure and a Si/Al ratio between about 40 to about 600, on which has been exchanged platinum ions and which has been impregnated with a rhenium compound such that the catalyst composition contains about 0.1 to about 0.5 wt. % platinum and rhenium, and which has been partially sulfided.

16. The process of claim 15 in which the catalyst component is composited with about 20 to about 80 wt. % alpha-alumina matrix.

17. The process of claim 16 in which the hydrocarbon conversion conditions comprise a temperature of about 300° to about 550° C., a pressure of about 1 to about 5 bar, a weight hourly space velocity of about 0.2 to about 50 hr$^{-1}$.

18. The process of claim 17 in which the selectivity to methane is less than about 3 wt. % and in which the selectivity to BTX hydrocarbons is greater than about 30 wt. %.

19. The process of claim 18 in which the feed comprises propane.

20. The process of claim 18 in which the feed comprises butane.

* * * * *

UNITED STATES PATENT AND TRADEMARK OFFICE
CERTIFICATE OF CORRECTION

PATENT NO. : 5,672,796
DATED : September 30, 1997
INVENTOR(S) : Gilbert Fernand Alphonse Froment, Wilfried Jozef Hippolyte Dehertog It is certified that error appears in the above-indentified patent and that said Letters Patent is hereby corrected as shown below:

Patent reads:

| Col. | Line | | | | |
|---|---|---|---|---|---|
| 3 | 7 | reads "$R_2O^3[R_2O^+ + M_2n^o]$" | | | |
| | | should read -- $R_2O^+/[R_2O^+ + M_{2/n}O]$ -- | | | |
| 7 | 62 | reads "6.6836     7     1.9482" | | | |
| | | should read --6.6836     7     1.9481-- | | | |
| 8 | 30 | (Table 1) reads "Feed   $C_3H_6$   $n$--$CH_{10}$   $n$--$C_6H_{14}$" | | | |
| | | should read --Feed   $C_3H_8$   $n$--$C_4H_{10}$   $n$--$C_6H_{14}$-- | | | |
| 8 | 36 | reads "Selectivity (31)" | | | |
| | | should read --Selectivity (3)-- | | | |
| 8 | 42 | reads "$C_3H_4$" | | | |
| | | should read --$C_3H_8$-- | | | |
| 8 | 43 | reads "$\Sigma C_4H_6$" | | | |
| | | should read --$\Sigma C_4H_8$-- | | | |

Signed and Sealed this

Fourth Day of August, 1998

Attest:

*Bruce Lehman*

BRUCE LEHMAN

*Attesting Officer*     *Commissioner of Patents and Trademarks*